United States Patent [19]

Sugawara et al.

[11] Patent Number: 5,114,920
[45] Date of Patent: May 19, 1992

[54] BU-3292T ANTIBIOTICS

[75] Inventors: Koko Sugawara, Saitama; Yuji Nishiyama; Koji Tomita, both of Tokyo; Masataka Konishi, Kawasaki; Toshikazu Oki, Yokohama, all of Japan

[73] Assignee: Bristol-Myers Squibb Co., New York, N.Y.

[21] Appl. No.: 244,225

[22] Filed: Sep. 14, 1988

[51] Int. Cl.$^5$ .................. A61K 37/02; C07K 7/00
[52] U.S. Cl. ........................... 514/11; 514/10; 530/317
[58] Field of Search ............ 514/9, 10, 11; 530/317, 530/318, 319, 320, 322

[56] References Cited

FOREIGN PATENT DOCUMENTS 61-1434  7/1986  Japan .................... 530/317

OTHER PUBLICATIONS

Meienhofer "Synthesis of actinomycin . . . " J. Am. Chem. Soc. 92(12) 3771-3777 (1970).
Meienhofer et al "Structure-Activity . . . " in Structure activity Relationship . . . ed. D. Perlman, 1977, pp. 488-494.

*Primary Examiner*—C. Warren Ivy
*Assistant Examiner*—Celia Chang
*Attorney, Agent, or Firm*—William T. Han

[57] ABSTRACT

New antibiotics designated BU-3292T A and B are provided which exhibit antimicrobial activity and also inhibit the growth of tumors in experimental animal systems. BU-3292T A is produced by fermentation of Elytrosporangium sp. nov. (ATCC 53784) while the BU-3292T B compound is obtained by oxidation of BU-3292T A.

3 Claims, 6 Drawing Sheets

BU-3292T ANTIBIOTICS

BACKGROUND OF THE INVENTION

1. Field of the Invention

This invention relates to novel antibiotic compounds designated BU-3292T A and B. The compounds possess antimicrobial and antitumor activities.

2. Description of the Prior Art

Elucidation of the structure of BU-3292T A revealed that it had a unique depsipeptide structure. This type of pentapeptide lactone has been proposed as a key intermediate in the biosynthesis of actinomycin (Katz. E: Antibiotics, Vol. II. Biosynthesis, p. 276, Springer-Verlay, Berlin, 1967), but none of such monomer type compound has so far been discovered in the microbial metabolites.

Actinomycin $Z_5$ (*Tetrahedron Letter*, 2567, 1973) and Schering 1a and 1b (15th Interscience Conference on Antimicrobial Agents and Chemotherapy, Abstract No. 419) are reported to each contain one mole of 5-methylproline. BU-3292T B differs from these actinomycins in that it has two moles of 5-methylproline forming two identical peptide lactone side chains.

SUMMARY OF THE INVENTION

The present invention provides the antibiotics BU-3292T A and B which exhibit activity against gram-positive bacteria and fungi. Additionally, the compounds exhibit in vitro and in vivo antitumor activity.

BU-3292T A is obtained by cultivating a BU-3292T-A-producing strain of Elytrosporangium sp. nov. in an aqueous nutrient medium containing assimilable sources of carbon and nitrogen under submerged aerobic conditions until a substantial amount of BU-3292T A is produced by said organism in said culture medium and then recovering the BU-3292T A from said culture medium. BU-3292T B may be produced by subjecting BU-3292T A to oxidation.

In another aspect there are provided pharmaceutical compositions useful for treating bacterial or fungal infections or tumors in an animal host comprising an effective bacterial-inhibiting, fungal-inhibiting or tumor-inhibiting amount of BU-3292T A or B together with a pharmaceutically acceptable carrier.

In a further aspect the present invention provides a method of treating bacterial or fungal infections in an animal host by administering to said host an effective antifungal or antibacterial amount of BU-3292T A or B, or a pharmaceutical composition thereof.

Finally, the present invention provides a method of inhibiting the growth of tumors in a mammalian host by administering to said host a tumor-inhibiting amount of BU-3292T A or B, or a pharmaceutical composition thereof.

DETAILED DESCRIPTION

The BU-3292T A antibiotic of the present invention is produced by fermentation of a BU-3292T-A-producing strain of Elytrosporangium. sp. nov. The preferred producing organism is a novel strain of a new species of Elytrosporangium designated herein as Elytrosporangium sp. nov. strain L703-4. This strain was isolated from a soil sample collected in Maharashtra State, India. A biologically pure culture of strain L703-4 has been deposited with the American Type Culture Collection (ATCC), Washington, D.C. and added to its permanent collection of microorganisms as ATCC 53784. The results of taxonomic studies revealed that strain L703-4 belongs to the genus Elytrosporangium and can be classified as a new species of that genus.

Strain L703-4 has the following properties:

Morphology

Both substrate and aerial mycelia are formed. The mycelia (0.5 μm in dia.) are long, well-branched and not fragmented into short filaments. Long chains of arthrospores are born monopodially on the aerial hyphae, which are straight, hook, or spiral with two turns (Retinaculiaperti) and include 8 to 20 spores per chain. Scanning electron micrography indicates that the spores are oval (0.8–1.0 by 1.2–1.8 μm in dia.), and have many warts on the surface. Short thick spore chains, which have 2 to 6 spores enclosed in a swollen rod-shaped sheath, are formed in the tip of substrate mycelium which penetrated agar medium only on a few agar media including Czapek-Dox sucrose-nitrate agar, glycerol asparagine agar and Bennett's agar.

Cultural characteristics

The growth is moderate on both natural organic media and chemically defined media. The ability of aerial mycelium forming on descriptive media is inferior to that of ordinary Streptomyces species. The aerial spore mass is gray to greenish gray. The reverse color is colorless to dark yellowish brown. Melanin and other distinct pigments are not formed.

Physiological characteristics

The growth occurs between 16° C. and 44° C., but not at 15° C. or 45° C. Tyrosinase production is negative. The tolerance to NaCl is observed at 8% w/v, but not at 10%. Among eleven diagnostic sugars for Streptomyces, ten sugars are utilized, but raffinose is not.

Cell chemistry

Whole cell hydrolysate contains LL-diaminopimelic acid, ribose, glucose and galactose, but not diagnostic sugars such as madurose, xylose or arabinose. Therefore, the strain belongs to cell wall Type I. The phospholipids contain phosphatidylethanolamine, phosphatidylglycerol and phosphatidylinositol, and hence is Type P-II.

Strain L703-4 forms chains of arthrospores on the aerial mycelium, along with mero-sporangium-like spore chains in the substrate mycelium and has a Type I cell wall and a Type P-II phospholipid. The major characteristics of Strain L703-4 are similar to those of the genus Streptomyces except for the formation of mero-sporangiumlike spore chains. According to the descriptions of Pridham and Tresner,[1] Strain L703-4 is placed in a species group; gray (GY) aerial mycelium, Spira (S) spore chain, absence of melanoid pigments (C-), and warty (WTY) spore wall ornamentation. Four species, S. atroolivaceus, S. cyanocolor, S. graminofaciens and S. griseoplanus are described in this species group. These species are different from Strain L703-4 in the absence of pod-shaped spore chain in substrate mycelium, the formation of longer spore chains and the absence of greenish-gray mycelium.

[1] Pridham, T. G. and H. D. Tresner: Genus Streptomyces Waksman and Henrici, 1943, P. 748-829. In R. E. Buchanan and N. E. Gibbons (ed.), Bergey's Manual of Determinative Bacteriology, 8th ed. 1974. The Williams & Wilkins Co., Baltimore.

The genus Elytrosporangium (Falcao et al. 1966)[2] forms long or short spore chains on the aerial mycelium as well as the pod-shaped spore chains in the substrate mycelium, while the genus Microellobospora (Cross and Lechevalier 1963)[2] bears pod-shaped spore chains both on the aerial and substrate mycelia without the formation of long spore chain. The spore chain morphology of Strain L703-4 is of the genus Elytrosporanogium, which includes four species, E. brasiliense,[3] E. carpinense,[3] E. spirale[3] and E. tokashikiense.[4]

[2] Cross, T. and M. Goodfellow: Taxonomy and classification of the actinomycetes. In: Actinomycetales: characteristics and practical importance (G. Sykes and F. A. Skinner, eds.), pp. 11-112, Academic Press (London) 1973. [3] Goodfellow, M., S. T. Williams and G. Alderson: Transfer of Elytrosporangium brasiliense Falcao de Morais et al., Elytrosporangium carpinense Falcao de Morais et al., Elytrosporangium spirale Falcao de Morais, Microellobosporia cinerea Cross et al., Microellobosporia flavea Cross et al., Microellobosporia grisea (Konev et al.) Pridham and Microellobosporia violacea (Tsyganov et al.) Pridham to the genus Streptomyces, with amended descriptions of the species. System. Appl. Microbiol. 8: 48-54, 1986.
[4] Japan Kokai Patent 60-192593 (Oct. 1, 1985). Antibiotic FR-900462. Fujisawa Pharmaceutical Ind. Co.

E. tokashikiense has warty or spiny spores, and the other three species have spores with smooth surface, and hence Strain L703-4 was compared to E. tokashikiense. As shown in Table 3, Strain L703-4 seems to be different from E. tokashikiense. Direct comparisons of Strain L703-4 to E. brasiliense ATCC 23727 indicated that both organisms have considerable resemblances in the cultural and physiological characteristics. However, as shown in Table 4, Strain L703-4 seems to have some significant differences in morphology and cultural and physiological properties from strain ATCC 23727. Thus, Strain L703-4 is considered to be a new species of Elytrosporangium. The designation *Elytrosporangium cucumerosporum*, sp. nov., is proposed for Strain L703-4 (cucumeris L.m. cucumber; cucumerosporum M.L.n. cucumber-shaped spore). Type strain is No L703-4 (single isolate). The genus Elytrosporangium and three species of the genus are described in Approved Lists of Bacterial Name [5] Recently, Goodfellow et al.[3] reported that the chemical, genetical and phenetic data indicate a close relationship between the genera Elytrosporangium, Microellobosporia and Streptomyces, and proposed that the genus Elytrosporangium becomes a junior synonym of the genus Streptomyces.

[5] Skerman, V. B. D., V. McGowan, and P. H. A. Sneath: Approved lists of bacterial names. Int. J. Syst. Bacteriol. 30: 225-420, 1980.

TABLE 1

Cultural characteristics of Strain L703-4.

| Medium | * | |
|---|---|---|
| Sucrose-nitrate agar (Czapek-Dox agar) | G | Moderate |
| | VM | Strong yellowish brown (74) |
| | AM | Rudimental; dark gray (266) |
| | DP | None |
| Tryptone-yeast extract broth (ISP No. 1) | G | Moderate, not turbid |
| | VM | Colorless |
| | AM | None |
| | DP | None |
| Yeast extract-malt extract agar (ISP No. 2) | G | Moderate |
| | VM | Deep yellowish brown (75) |
| | AM | Moderate; olive gray (113) |
| | DP | Strong yellowish brown (74) |
| Oat meal agar (ISP No. 3) | G | Poor to moderate |
| | VM | Dark yellowish brown (78) |
| | AM | Moderate; olive gray (113) |
| | DP | None |
| Inorganic salts-starch agar (ISP No. 4) | G | Poor |
| | VM | Colorless |
| | AM | Scant; olive gray (113) |
| | DP | None |
| Glycerol-asparagine agar (ISP No. 5) | G | Moderate |
| | VM | Deep yellowish brown (75) |
| | AM | Moderate; greenish gray (155) |
| | DP | None |
| Peptone-yeast extract-iron agar (ISP No. 6) | G | Poor |
| | VM | Colorless |
| | DP | Strong yellow (84) |
| Tyrosine agar (ISP No. 7) | G | Poor |
| | VM | Medium yellowish brown (77) |
| | AM | Poor; yellowish gray (93) |
| | DP | None |
| Glucose-asparagine agar | G | Poor |
| | VM | Colorless |
| | AM | None |
| | DP | None |
| Nutrient agar | G | Poor |
| | VM | Colorless |
| | AM | None |
| | DP | None |
| Bennett's agar | G | Poor |
| | VM | Deep yellowish brown (75) |
| | AM | Scant; light olive gray (94) |
| | DP | Light olive yellow (94) |
| Papavizas' V-8 juice-dextrose-yeast extract agar | G | Moderate |
| | VM | Deep yellowish brown (75) |
| | AM | Poor; deep greenish gray (156) |
| | DP | Strong yellowish brown (74) |

Observations after incubation at 28° C. for 3 weeks.
Color and number in parenthesis follow ISCC-NBS designation.
*Abbreviations: G-growth; VM-color of vegetative mycelium; AM-aerial mycelium; DP-diffusible pigment

TABLE 2

Physiological characteristics of Strain L703-4

| Hydrolysis of: | | Utilization of**: | |
|---|---|---|---|
| | | Glycerol | + |
| Gelatin | + | D-Arabinose | − |
| Starch | + | D-Xylose | + |
| Milk coagulation: | − | D-Ribose | + |
| Peptonization | − | L-Rhamnose | + |
| Production of: | | D-Glucose | + |
| Nitrate reductase | +, −* | D-Galactose | + |
| Tyrosinase | + | D-Fructose | + |
| Tolerance to: | | D-Mannose | + |
| Lysozyme, 0.01% | + | L-Sorbose | − |
| NaCl, 1-8% | + | Sucrose | + |
| 10% | − | Lactose | + |
| pH 4.3-11.8 | + | Cellobiose | + |
| Temperature | | Melibiose | |
| Growth range | 16° C.-44° C. | Trehalose | + |
| Optimal growth | 31° C.-42° C. | Raffinose | − |
| No growth | 15° C. and 45° C. | D-Melezitose | − |
| | | Soluble starch | + |
| | | Cellulose | − |
| | | Dulcitol | − |
| | | Inositol | + |
| | | D-Mannitol | + |
| | | D-Sorbitol | ± |
| | | Salicin | − |

*Positive in Czapek's sucrose-nitrate broth, and negative in peptone-nitrate broth
**Basal medium: Pridham-Gottlieb's inorganic medium (ISP Med. No. 9)

TABLE 3

Differential characteristics of Strain L703-4 and
*Elytrosporangium tokashikiense*

|  | Strain L703-4 | *E. tokashikiense* |
|---|---|---|
| Color of aerial mycelium: | | |
| ISP medium No. 3 | Olive gray | Pale brown |
| No. 4 | Olive gray | Pale cinnamon-pink or gray |
| No. 5 | Greenish gray | Pale yellow-orange |
| Growth temperature range | 16–44° C. | 18–34° C. |
| Utilization of carbon sources: | | |
| D-Xylose | + | − |
| L-Arabinose | + | − |
| L-Rhamnose | + | − |
| Raffinose | + | − |

TABLE 4

Differential characteristics of Strain L703-4 and *E. brasiliense* ATCC 23727

|  | Strain L703-4 | *E. brasiliense* Strain ATCC 23727 |
|---|---|---|
| Morphology: Spore surface | Warty | Smooth |
| Cultural characteristics: | | |
| Czapeck's sucrose-nitrate agar | Moderate growth | No growth |
| Reverse color: ISP media nos. 2, 3 and 5 | Yellowish brown | Dark olive gray |
| Growth temperature range | 16–44° C. | 15–38° C. |
| Utilization of carbon source: | | |
| Sucrose | + | − |
| Raffinose | − | + |

It is to be understood that the present invention is not limited to use of the preferred strain L703-4 described above or to organisms fully answering the above descriptions. It is especially intended to include other BU-3292T-A-producing variant or mutant strains of the said organism which can be produced by conventional means such as x-radiation, ultraviolet radiation, treatment with nitrogen mustards, phage exposure, and the like.

Preparation of BU-3292T A

BU-3292T A is produced by cultivating a BU-3292T A-producing strain of Elytrosporangium sp. nov., preferably a strain having the characteristics of Elvtrosporangium sp. nov. strain L703-4 (ATCC 53784) or a variant or mutant thereof, under submerged aerobic conditions in an aqueous nutrient medium. The producing organism is grown in a nutrient medium containing an assimilable carbon source, for example, glycerol, L-arabinose, D-xylose, D-ribose, D-glucose, D-fructose, D-mannose, sucrose, cellobiose or soluble starch. The nutrient medium should also contain an assimilable nitrogen source such as fish meal, peptone, soybean flour, peanut meal, cottonseed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate, or like ions.

Production of BU-3292T A can be effected at any temperature conducive to satisfactory growth of the organism, e.g. 16° C. to 44° C., and is conveniently carried out at a temperature of about 28° C.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of BU-3292T A. The medium in which the vegetative inoculum is produced can be the same as, or different from, that utilized in the tank as long as it is such that a good growth of the producing organism is obtained.

In general, optimum production of BU-3292T A is achieved after incubation periods of about 2–5 days. Antibiotic production may be monitored by the paper disc-agar diffusion assay using *Bacillus subtilis* M45 (rec−) as the test organism or in vitro cytotoxic assay against B16 melanomic cells.

Isolation and Purification

BU-3292T A may be isolated from the fermentation broth by conventional isolation and purification procedures, e.g. solvent extraction and chromatography. Example 2 below illustrates a preferred isolation and purification procedure for obtaining BU-3292T A in substantially pure form.

Preparation of BU-3292T B

BU-3292T B is produced by subjecting BU-3292T A to oxidizing conditions, either by allowing the BU-3292T A to stand at room temperature in an inert solvent for a sufficient time to allow conversion to BU-3292T B, or by reacting BU-3292T A in an inert solvent, e.g. a $C_1$–$C_6$ alkanol, acetonitrile, dimethylformamide, dioxane, water, pH 6–8 buffer, or a mixture thereof, with a suitable oxidizing agent such as $O_2$, $MnO_2$, $K_3Fe(CN)_6$, $Pb(OAc)_2$, $FeCl_3$, etc. The reaction is preferably carrried out at a temperature in the range of about 0°–80° C. A preferred process comprises reacting BU-3292T A with $K_3Fe(CN)_6$ in a solvent system consisting of $CH_3OH$: pH 7.1 phosphate buffer (1:1 v/v) at room temperature.

Physicochemical Properties of BU-3292T A & B

Figure 1:
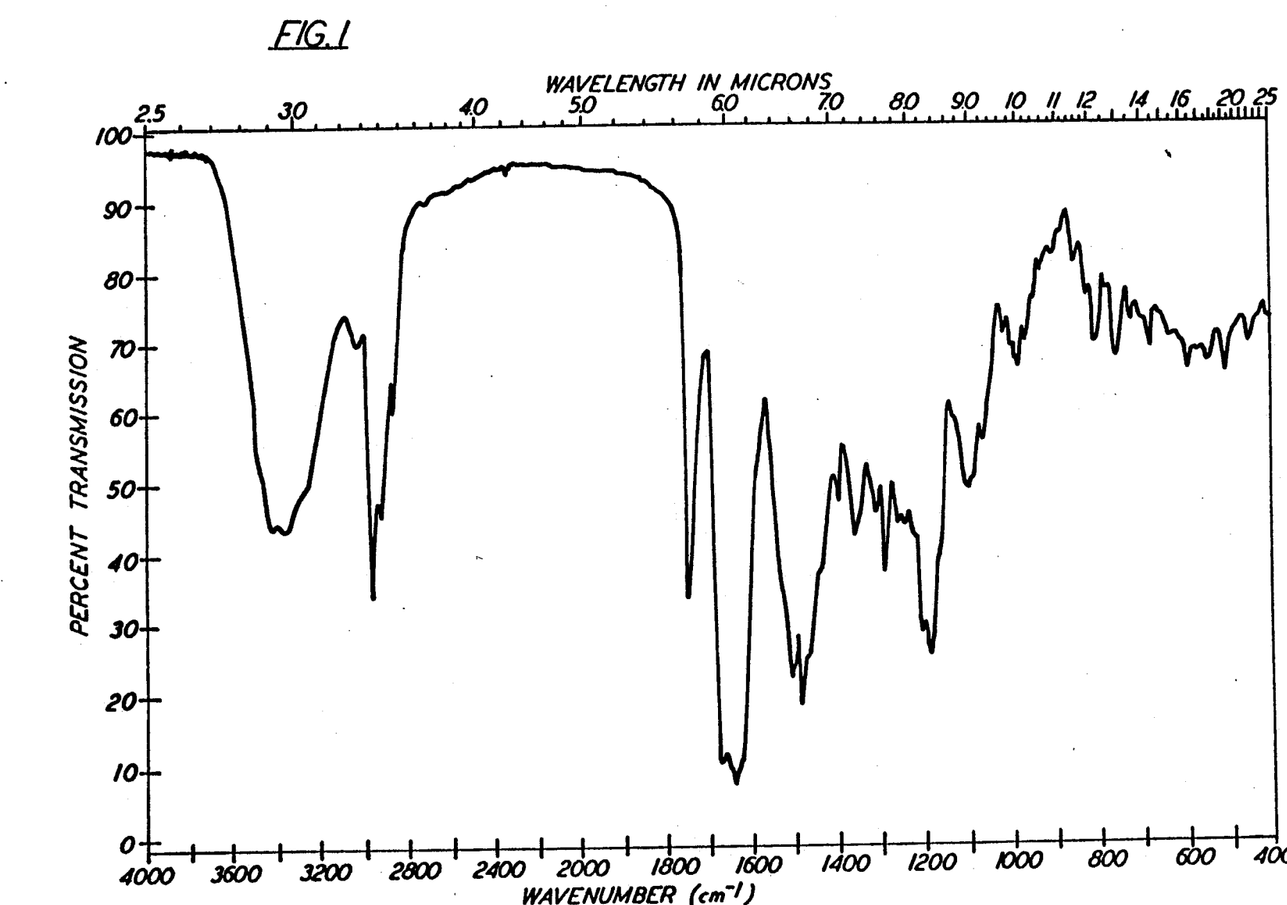
FIG. 1 represents the infrared absorption spectrum of BU-3292T A (KBr).
Figure 2:
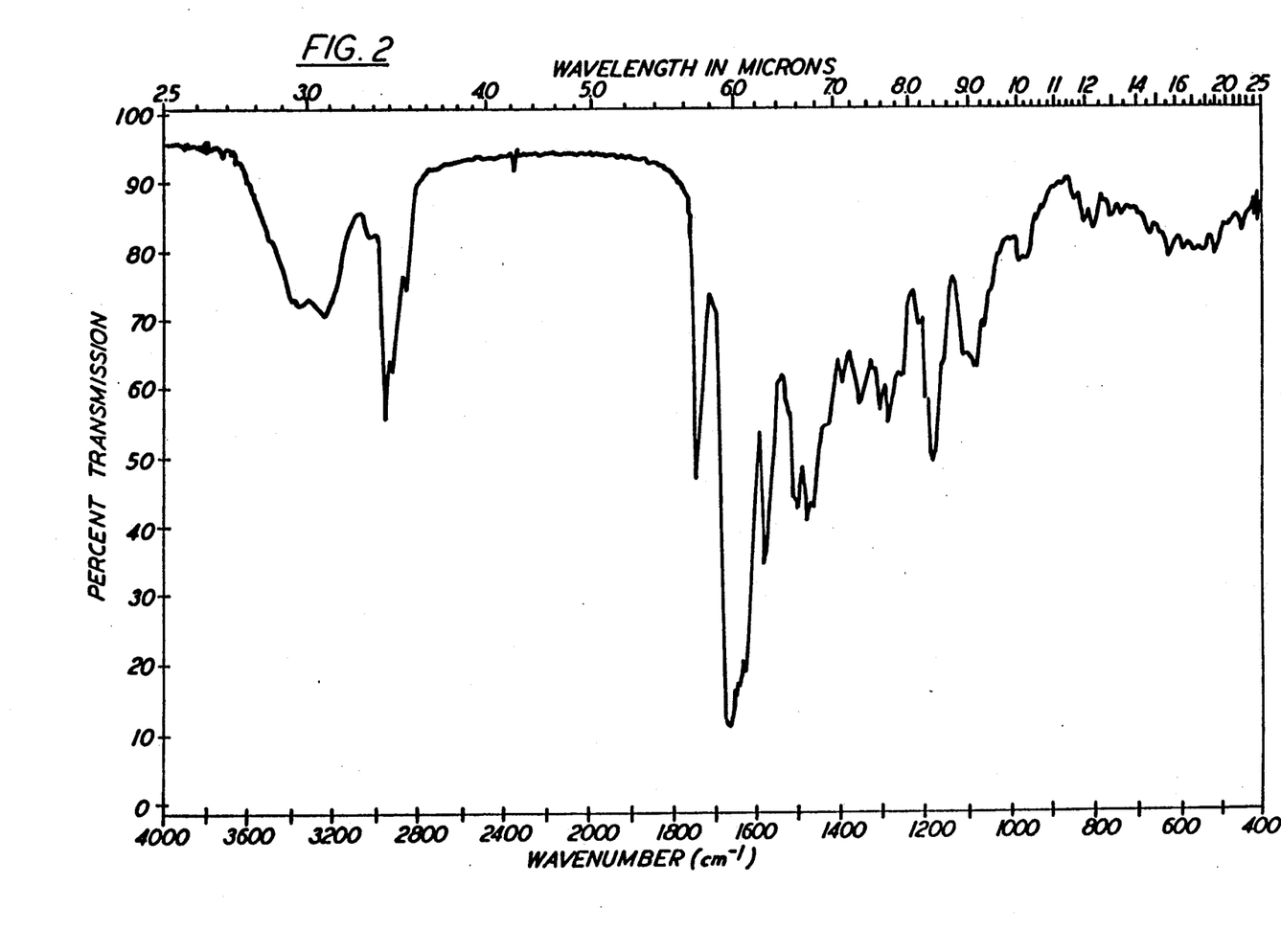
FIG. 2 represents the infrared absorption spectrum of BU-3292T B (KBr).
Figure 3:
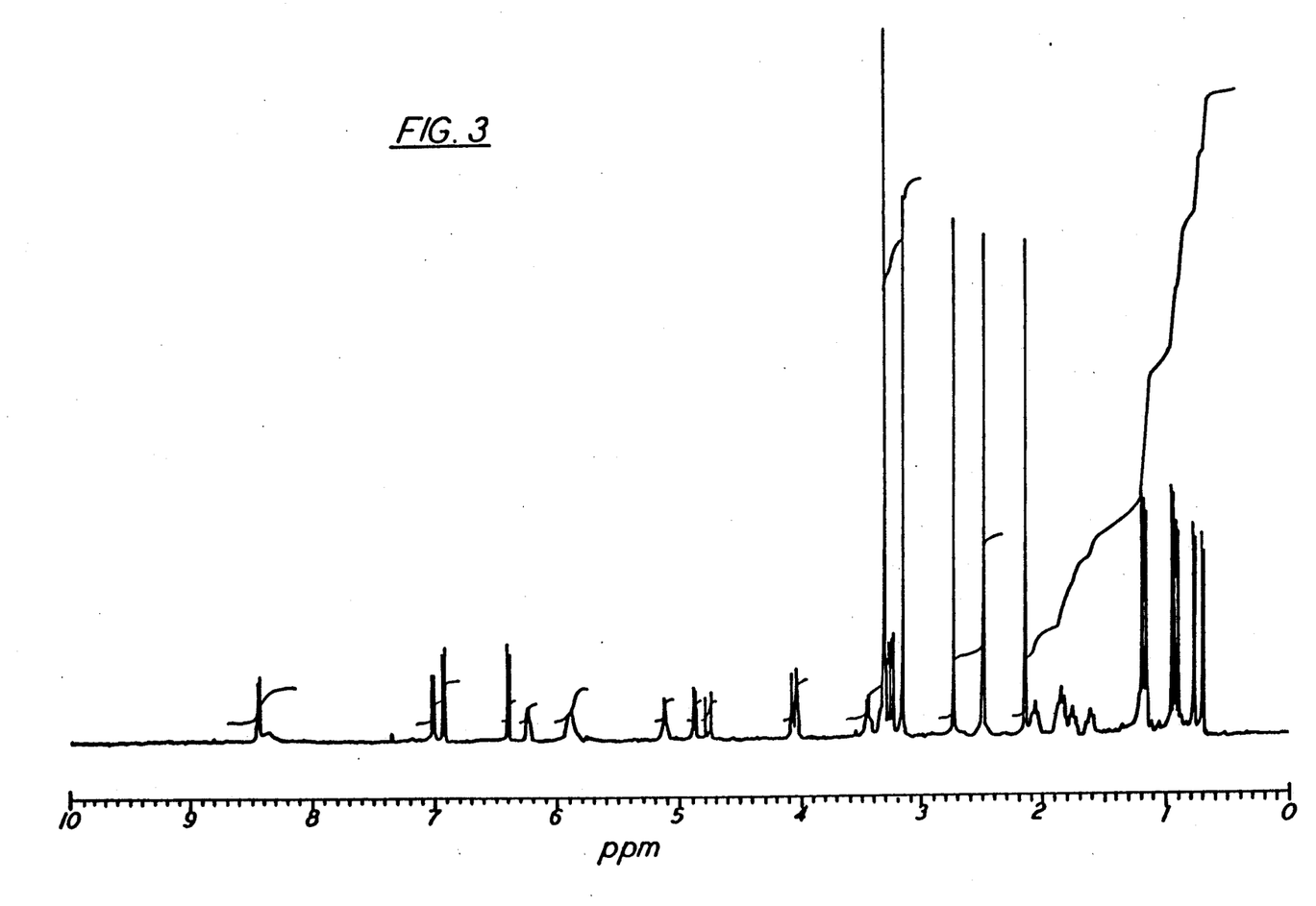
FIG. 3 represents the $^1$H-NMR spectrum of BU-3292T A (400 MHz in DMSO-$d_6$).
Figure 4:
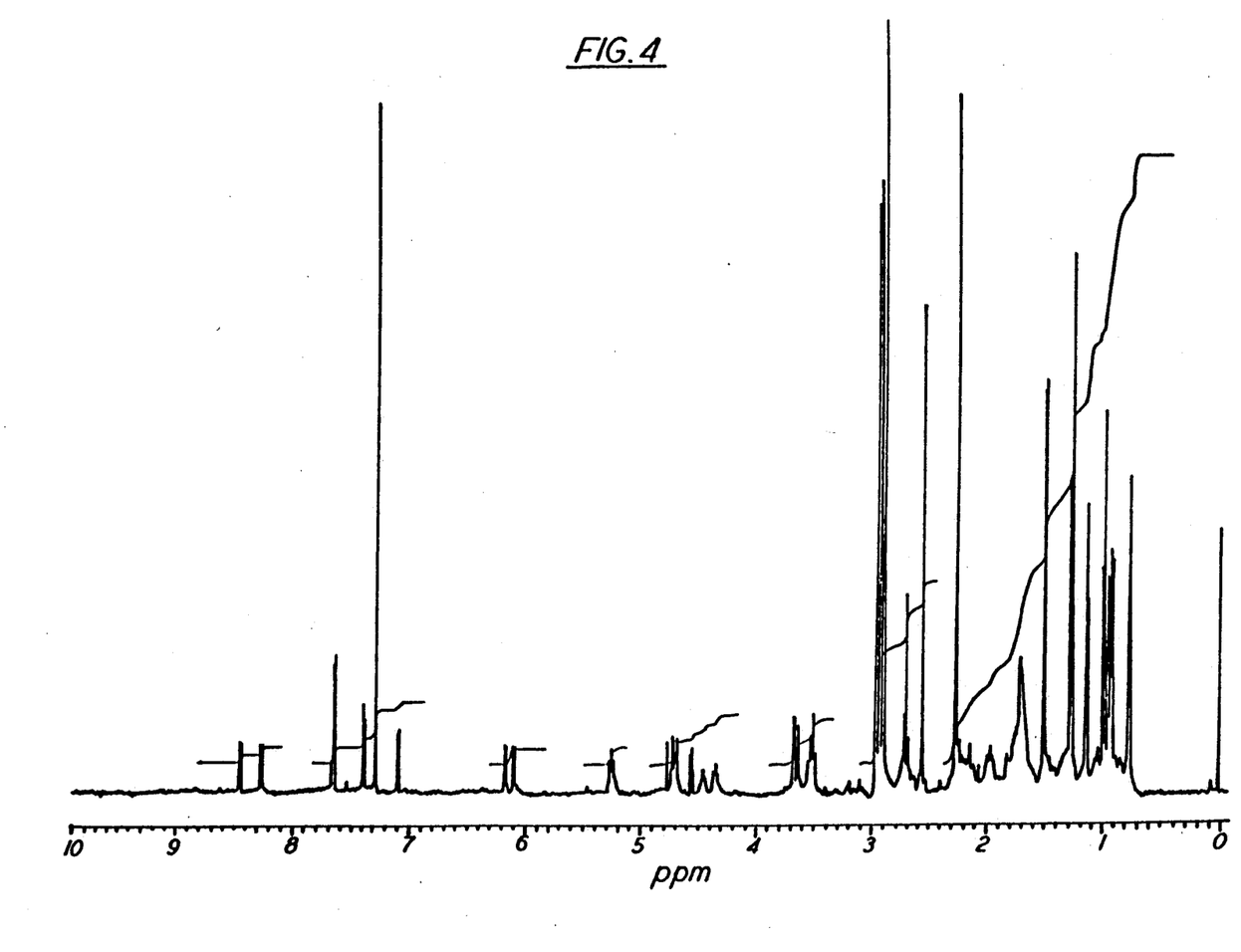
FIG. 4 represents the $^1$H-NMR spectrum of BU-3292T B (400 MHz in CDCl$_3$, TMS reference).
Figure 5:
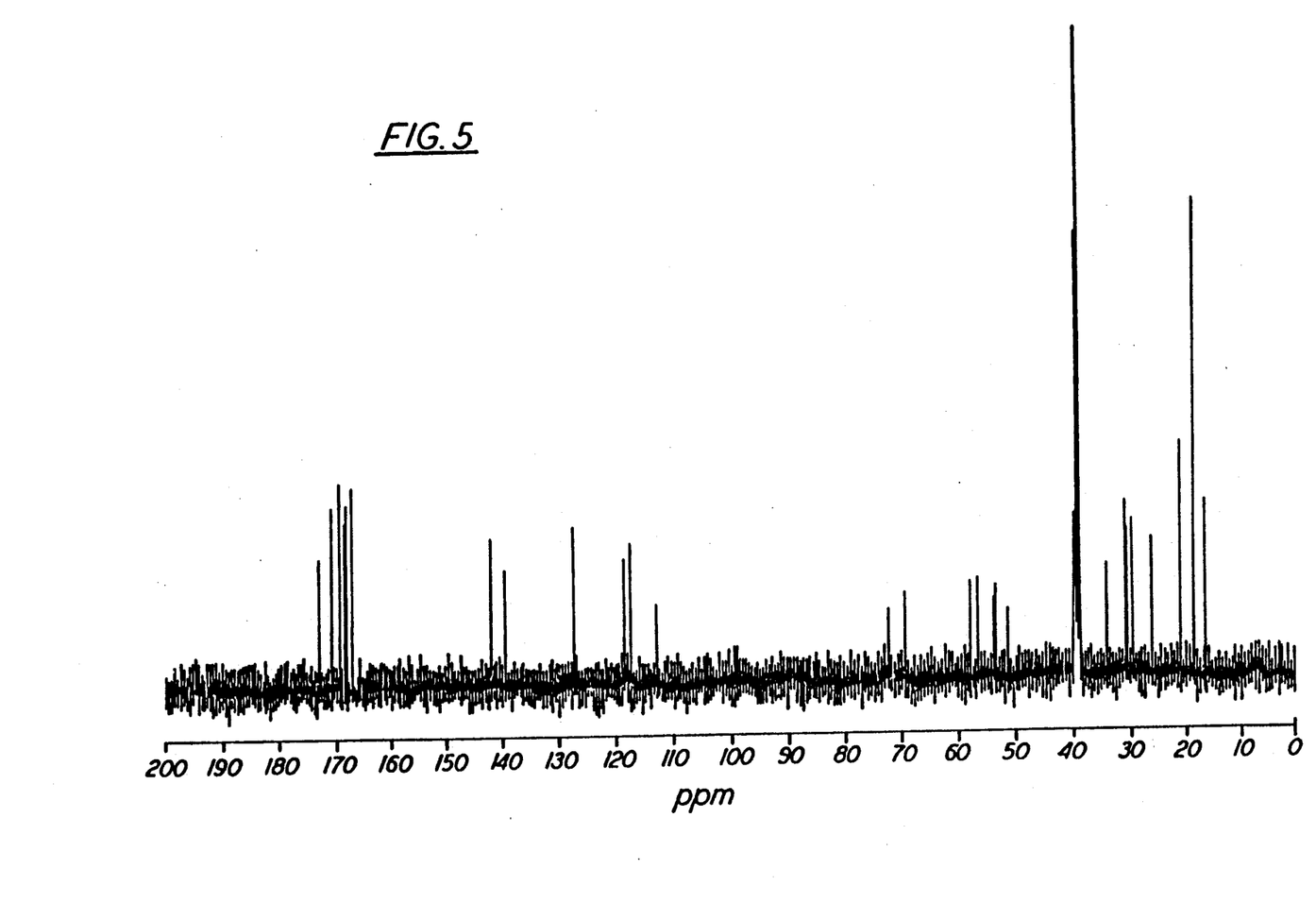
FIG. 5 represents the $^{13}$C-NMR spectrum of BU-3292T A (100 MHz in DMSO-$d_6$).
Figure 6:
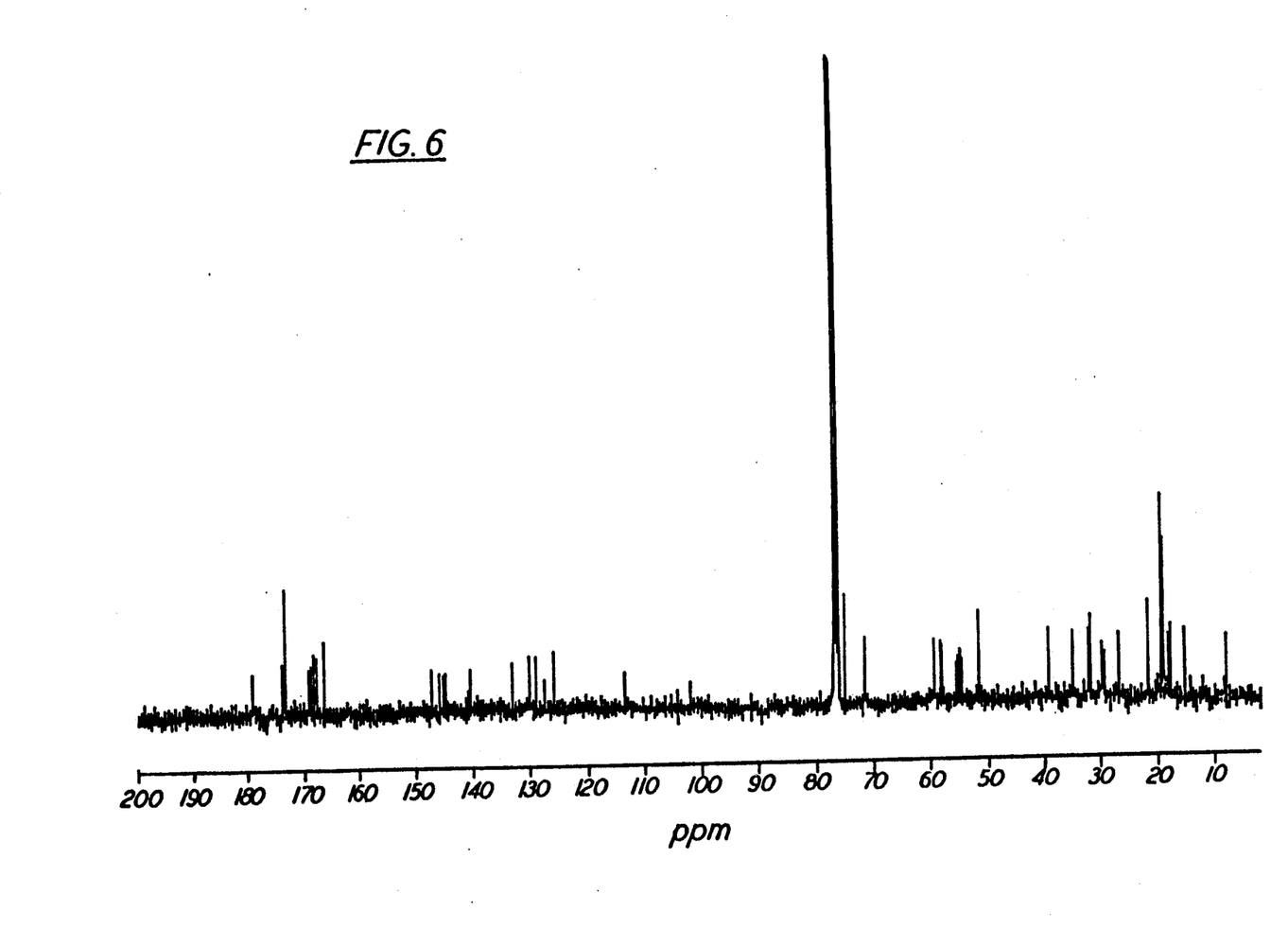
FIG. 6 represents the $^{13}$C-NMR spectrum of BU-3292T B (100 MHz in CDCl$_3$).

The physicochemical properties of BU-3292T A and B are summarized in Table 5 below. BU-3292T A is isolated as a white amorphous powder, while BU-3292T B is an orange-red powder. Both compounds are readily soluble in dimethyl sulfoxide, dimethylformamide, methanol, ethyl acetate and chloroform, but insoluble in water and other organic solvents. The compounds give positive responses to iodine and Rydone-Smith reagents, but negative responses to Sakaguchi, ferric chloride, ninhydrin and anthrone reagents. The UV spectrum of BU-3292T A shows absorption maxima at 217, 257 and 329 nm in methanol solution, suggesting the anthranilic acid type chromophore. BU-3292T B exhibits a UV spectrum similar to those of the actinomycins. The IR spectra of BU-3292T A and B are illustrated in FIGS. 1 and 2, respectively. The proton NMR of Bu-3292T A and B are shown in FIGS. 3 and 4 and $^{13}$C-NMR of BU-3292T A and B are shown in FIGS. 5 and 6.

TABLE 5
Physicochemical properties of BU-3292T A and B

| | BU-3292T A | BU-3292T B |
|---|---|---|
| Nature | White amorphous powder | Orange-red powder |
| M.p. | 193–195° C. (decomp.) | 248–250° C. |
| $[\alpha]_D^{24}$ | $-21° \pm 2°$ | $[\alpha]_D^{25} -223° \pm 2°$ |
| | (c 0.5, MeOH) | (c 0.23, MeOH) |
| UV $\lambda_{max}$nm ($E_{1cm}^{1\%}$) | 217(493),257$^{sh}$(111), | 206(408),237(227), |
| in MeOH | 329(56) | 422$^{sh}$(137) |
| in 0.01N HCl—MeOH | 207(635),249$^{sh}$(131), | 206(408),237(227), |
| | 290(42) | 422$^{sh}$(137) |
| in 0.01N NaOH—MeOH | 210(429),246(299), | 206(408),237(227), |
| | 277$^{sh}$(90),343(50) | 422$^{sh}$(137) |
| Microanalysis Found | C 59.75 | 58.42 |
| | H 7.58 | 7.17 |
| | N 11.10 | 11.43 |
| Calcd for | $C_{32}H_{48}N_6O_8$ | $C_{64}H_{90}N_{12}O_{16} \cdot 2H_2O$ |
| | C 59.61 | 58.25 |
| | H 7.50 | 7.18 |
| | N 13.03 | 12.74 |
| MS m/z | 644 (M$^+$, EI) | 1283 (M$^+$ + 1, SIMS) |
| HREIMS | $C_{32}H_{48}N_6O_8$ (M$^+$; obsd m/z 644.3489, calcd m/z 644.3532) | |
| TLC SiO$_2$ EtOAc—MeOH (4:1) | Rf 0.55 | 0.58 |
| CH$_2$Cl$_2$—MeOH (9:1) | 0.43 | 0.64 |

Structure of BU-3292T A

The $^{13}$C-NMR spectrum of BU-3292T A demonstrated 32 carbons including seven C—CH$_3$, two N—CH$_3$, three methylene, eight methine, two —CH=, four =C< and six >C=O carbons. These data coupled with the high resolution EI-MS (M$^+$:m/z 644.3489) and microanalysis allowed us to assign a molecular formula of $C_{32}H_{48}N_6O_8$ for BU-3292T A. The IR spectrum exhibited strong absorption at 3400, 2950, 1750, 1640, 1480 and 1200 cm$^{-1}$, suggesting that BU-3292T A had a depsipeptide structure. The UV absorption maximum at 329 nm in methanol shifted to 290 nm in acidic solution and to 343 nm in alkaline solution indicating the presence of a hydroxy anthranilic acid moiety in BU-3292T A. When hydrolyzed with 6N hydrochloric acid, BU-3292T A gave five amino acids, threonine, valine, sarcosine, N-methylvaline and an unidentified amino acid as determined by the amino acid analysis and TLC. All of the protons and carbons observed in $^1$H and $^{13}$C-NMR spectra of BU-3292T A were unambiguously assigned using $^1$H—$^1$H and $^{13}$C-$^1$H correlated NMR spectra. These spectra clearly showed that the unidentified amino acid was 5-methylproline. The connectivities of the amino acids and the chromophore of BU-3292T A were established by $^{13}$C—$^1$H long range COSY spectrum, and the structure of A was established as shown below.

As described before, BU-3292T B was prepared from BU-3292T A by oxidation with potassium ferricyanide. It showed the UV, IR and $^1$H-NMR spectra similar to those of the known actinomycin group antibiotics. Thus the structure of BU-3292T B was determined as shown below.

Biological Activity of BU-3292T A and B

Antimicrobial activity

The antimicrobial activity of BU-3292T A and B was determined against aerobic and anaerobic bacteria and fungi by a serial two-fold agar dilution method. Actinomycin D was tested as the reference and the results are shown in Table 6. BU-3292T A and B are active against aerobic gram-positive bacteria, and weakly active against anaerobic gram-negative bacteria and fungi. However, they are inactive against gram-negative bacteria. The minimum inhibitory concentration (MIC) values of BU-3292T A are comparable to those of BU- 3292T B, and about one-fourth those of actinomycin D.

TABLE 6

Antimicrobial activity of BU-3292T A and B

| Test Organisms | Test medium* | MIC (mcg/ml) | | |
|---|---|---|---|---|
| | | BU-3292T A | BU-3292T B | Actinomycin D |
| Staphylococcus aureus 209P | A | 1.6 | 1.6 | 0.4 |
| Staphylococcus aureus smith | A | 1.6 | 1.6 | 0.4 |
| Staphylococcus epidermidis D153 | A | 1.6 | 1.6 | 0.4 |
| Streptococcus faecalis A9612 | A | 0.8 | 0.8 | 0.1 |
| Streptococcus pyogenes A20201 | A | 1.6 | 0.8 | 0.2 |
| Micrococcus luteus 1001 | A | 0.4 | 0.4 | 0.2 |
| Bacillus subtilis PCI-219 | A | 0.4 | 0.8 | 0.2 |
| Escherichia coli NIHJ | A | >100 | >100 | >100 |
| Klebsiella pneumoniae D11 | A | >100 | 100 | 25 |
| Pseudomonas aeruginosa A9930 | A | >100 | >100 | 100 |
| Proteus vulgalis A9436 | A | >100 | >100 | >100 |
| Proteus mirabilis A9554 | A | >100 | >100 | >100 |
| Bacteroides fragilis A22693 | B | >100 | >100 | >100 |
| Clostridium difficile A21675 | B | >100 | >100 | 25 |
| Clostridium perfringens A9635 | B | 100 | 25 | 6.3 |
| Propionibacterium acnes A21933 | B | 100 | 12.5 | 6.3 |
| Propionibacterium anaerobius A21905 | B | 100 | 6.3 | 1.6 |
| Candida albicans IAM 4888 | C | >100 | >100 | >100 |
| Cryptococcus neoformans IAM 4519 | C | 100 | >100 | >100 |
| Aspergillus fumigatus IAM 2530 | C | >100 | >100 | >100 |
| Trichophyton mentagrophytes D155 | C | >100 | >100 | >100 |
| Fusarium moniliforme A2284 | C | >100 | 50 | >100 |
| Mucor spinosus IFO 5317 | C | 12.5 | 25 | >100 |

*A: Nutrient agar, B: GAM agar, C: Sabouraud dextrose agar

Antifungal activity

Table 6 also indicates that BU-3292T A and B exhibit activity against certain fungi. For example BU-3292T A shows an MIC of 12.5 μg/ml when tested in vitro against Mucor spinosus IF05317 and BU-3292T B demonstrates an MIC of 25 for this organism. In contrast, actinomycin D exhibits an MIC of >100 for this test organism. BU-3292T B also shows in vitro activity against Fusarium moniliforme.

Antitumor activity

BU-3292T components A and B were tested for in vitro cytotoxicity against murine and human tumor cells and for in vivo antitumor activity in mice. Actinomycin D was used as a reference compound in both in vitro and in vivo experiments. B16-F10 (murine melanoma) and Moser (human colorectal carcinoma) cells were grown to the logarithmic phase in enriched Eagle minimum essential medium (MEM) supplemented with fetal calf serum (FCS, 10%) and kanamycin (60 mcg/ml), harvested and inoculated into wells of a 96-well microtiter plate with test materials at the concentrations of $3.0 \times 10^4$ and $6.0 \times 10^4$ cells/ml, respectively. They were incubated at 37° C. in humidified atmosphere of 5% $CO_2$ and 95% air for 72 hours. The cytotoxic activity was determined colorimetrically at 540 nm after staining viable cells with neutral red. The results are summarized in Table 7. Both components A and B were highly cytotoxic, but the latter was more potent than the former in the in vitro cytotoxicity experiments. Their activities were approximately 10 and 400 times stronger against B16-FIO cells than against Moser cells, respectively. Inhibitory effects of BU-3292T component A on macromolecule (DNA, RNA and protein) synthesis were determined in vitro. Cultured L1210 murine leukemia cells ($5 \times 10^5$ cells/ml) were incubated with test materials at 37° C. for 15 minutes and then further incubated for 60 minutes after the addition of labelled precursor, $^3H$-thymidine, $^{14}C$-uridine or $^3H$-leucine, into the cultured mixtures. After washing with chilled 5% trichloroacetic acid solution, the radioactivity incorporated into the acid-insoluble fraction of the tumor cells was determined in a liquid scintillation counter. As shown in Table 8, BU-3292T component A inhibited RNA synthesis approximately 300 times more than DNA synthesis, whereas the compound showed no inhibitory effect on protein synthesis at 100 mcg/ml, the highest concentration tested. In vivo antitumor activities of BU-3292T components A and B were tested in tumor-bearing female CDF mice. After the intraperitoneal implantation of diluted ascitic fluid with $1.0 \times 10^6$ lymphocytic leukemia P388 cells into the mice, test compounds were administered intraperitoneally once a day on days 1, 2 and 3 (QD×3). Both BU-3292T components A and B demonstrated fairly good anti-P388 leukemic activity with maximum T/C values of 160%, similar to that of actinomycin D (Table 9).

TABLE 7

In vitro cytotoxicities against B16-F10 melanoma and Moser cells

| Compound | IC$_{50}$ (mcg/ml) | |
|---|---|---|
| | B16-F10 | Moser |
| BU-3292T A | 0.007 | 0.09 |
| BU-3292T B | <0.00016 | 0.06 |
| Actinomycin D | 0.002 | 0.9 |

TABLE 8

Inhibition of macromolecule synthesis in L1210 leukemia cells

| Compound | IC$_{50}$ (mcg/ml) | | |
|---|---|---|---|
| | DNA | RNA | Protein |
| BU-3292T A | 80 | 0.23 | >100 |
| Actinomycin D | 8.1 | 0.17 | >100 |

TABLE 9

Antitumor activity of BU-3292T against P388 leukemia (ip)

| Compound | Dose*[1] (mg/kg/day) | MST*[2] (day) | T/C (%) | Body weight change on day 4 (g) |
|---|---|---|---|---|
| BU-3292T A | 30 | Tox | Tox | — |
| | 10 | 16.0 | 160*[3] | −3.0 |
| | 3 | 14.0 | 140*[3] | +0.3 |
| | 1 | 13.0 | 130*[3] | +0.5 |
| | 0.3 | 12.0 | 120 | +1.3 |
| | 0.1 | 11.0 | 110 | +1.3 |
| | 0.03 | 11.0 | 110 | +1.3 |
| BU-3292T B | 1 | Tox | Tox | — |
| | 0.3 | 8.0 | 80 | −3.3 |
| | 0.1 | 16.0 | 160*[3] | −1.0 |
| | 0.03 | 14.0 | 140*[3] | +1.0 |
| | 0.01 | 12.0 | 120 | +1.0 |
| | 0.003 | 11.0 | 110 | +1.0 |
| Actinomycin D | 0.3 | 7.0 | 70 | −3.5 |
| | 0.1 | 16.0 | 160*[3] | −2.0 |
| | 0.03 | 15.0 | 150*[3] | +0.5 |
| | 0.01 | 14.0 | 140*[3] | +1.3 |
| | 0.003 | 13.5 | 135*[3] | +1.0 |
| | 0.001 | 11.0 | 110 | +1.3 |
| Vehicle | — | 10.0 | — | +1.5 |

*[1] QD × 3, ip
*[2] Median survival time
*[3] Significant antitumor effect (T/C ≧ 125%)

As shown above BU-3292T A and B possess antibacterial and antifungal activity and are thus useful in the therapeutic treatment of mammals and other animals for diseases caused by such organisms. Additionally, the compounds may be utilized for other conventional applications of antimicrobial agents such as disinfecting medical and dental equipment.

The in vitro and in vivo antitumor data presented above indicate that BU-3292T A and B are also therapeutically useful in inhibiting the growth of malignant tumors in mammalian hosts.

The present invention, therefore, provides a method for therapeutically treating an animal host affected by a bacterial or fungal infection which comprises administering to said host an effective antibacterial or antifungal dose of BU-3292T A or B, or a pharmaceutical composition thereof.

Also provided is a method for inhibiting the growth of malignant tumors in mammals which comprises administering to said mammalian host an effective tumor-inhibiting dose of BU-3292T A or B, or a pharmaceutical compositon thereof.

In another aspect the present invention provides a pharmaceutical composition which comprises an effective antibacterial or antifungal amount of BU-3292T A or B in combination with an inert pharmaceutically acceptable carrier or diluent.

Additionally, the invention provides a pharmaceutical composition which comprises an effective tumor-inhibiting amount of BU-3292T A or B in combination with an inert pharmaceutically acceptable carrier or diluent.

The pharmaceutical compositions may contain other active antimicrobial or antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparation for parenteral administration such as sterile solutions, suspensions or emulsions. They may also be manufactured in the form of sterile solid compositions which can be dissolved in sterile water, physiological saline or some other suitable sterile injectable medium immediately before use.

For use as an antimicrobial agent, the BU-3292T A or B, or pharmaceutical composition thereof, is administered so that the concentration of active ingredient is greater than the minimum inhibitory concentration for the particular organism being treated. For use as an antitumor agent, optimal dosages and regimens of BU-3292T A or B for a given mammalian host can be readily ascertained by those skilled in the art. It will, of course, be appreciated that the actual dose of compound used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

EXAMPLE 1

Fermentation of BU-3292T A

A well-grown agar slant of Elytrosporangium sp. Strain No. L703-4, was used to inoculate into a 500-ml Erlenymeyer flask containing 100 ml of vegetative medium consisting of 2% soluble starch (Nichiden Kagaku), 1% Pharmamedia (Traders Protein), 0.003% $ZnSO_4 \cdot 7H_2O$ and 0.4% $CaCO_3$, the pH being adjusted to 7.0 before sterilization. The flask was shaken at 28° C. for 4 days on a rotary shaker (200 rpm) and 5 ml of the culture was transferred into an Erlenmeyer flask containing 100 ml of fermentation medium having the same composition as the vegetative medium described above. The fermentation was carried out at 28° C. for 4 to 5 days with shaking on a rotary shaker. The antibiotic titer in fermentation broths were determined by the paper disc agar diffusion assay using Bacillus subtilis M45 (rec−) as the test organism and in vitro cytotoxic activity against B16 melanoma cells.

The fermentation was also carried out in a tank fermentor. A 2-liter portion of the vegetative culture by flask fermentation was inoculated into a 200-liter tank fermentor containing 120 liters of the fermentation medium. Fermentation was run at 28° C. with agitation at 250 rpm and aeration rate of 120 liters per minute.

The productivity could be monitored by TLC scanning (330 nm) (Shimadzu-Dual Wave Length TLC scanner CS-910). The concentrate of ethyl acetate extract from the broth filtrate was spotted on TLC plate RP-18 $F_{254}S$ (Merck Co.) and developed with 70% aq. methanol. The antitumor activity reached a maximum of 2 μg/ml after 50 hrs fermentation.

EXAMPLE 2

Isolation and Purification of BU-3292T A

The cultured broth (220 liters, pH 7.3) was separated into the mycelial cake and the supernate by using a Sharpless-type centrifuge. The supernate (205 liters) was extracted with n-BuOH (80 liters) and the extract was concentrated to an aqueous solution (1 liter). The solution was then extracted two times with ethyl acetate (1 liter each). Evaporation of the extract gave a crude solid which was chromatographed on a column of Diaion HP-20 (Mitsubishi Chem. Industries, Tokyo, 4.0×75cm) with elution of 50% aqueous methanol (3 liters) and then 80% aqueous methanol (5 liters). The fractions eluted were monitored by paper disc assay using *B. subtilis* M45 (Rec⁻) as the test organism The active fractions eluted with 80% aqueous methanol were pooled and concentrated to afford an oily residue. This solid was dissolved in acetone (10 ml) and the solution was added dropwise into n-hexane (1 liter) to deposit an oily precipitate (2.8g). This solid was applied on a column of silica gel (2.2×75cm) which had been pre-washed with methylene chloride. The elution was performed by a methylene chloride-methanol mixture with stepwise increase of methanol concentration (2–10%, v/v). The first active fractions eluted with 2% methanol were collected and concentrated in vacuo to afford the actinomycin complex. The second active fractions eluted with 5% methanol were combined and evaporated to yield a crude solid of BU-3292T A (1.1 g). This crude solid was further chromatographed on Lichroprep RP-18 (Merck, 2.2×70cm) by successive elution with 30% methanol, 50% methanol and 80% methanol. Bio-active fractions eluted with 50% methanol were combined and concentrated in vacuo to afford a semi-pure solid of BU-3292T A (224 mg). This solid was charged on a column of silica gel which had been pre-washed with methylene chloride. Elution with methylene chloride-methanol (96:4, v/v) gave active compound, which was further purified by Sephadex LH-20 (2.2×70 cm) developed with methanol to afford a homogeneous solid of BU-3292T A (48 mg).

EXAMPLE 3

Preparation Of BU-3292T B

A solution of BU-3292T A (20 mg) in methanol (5 ml) was added to a stirred solution of potassium ferricyanide (30 mg) in 0.067 M phosphate buffer (pH 7.1, 5 ml). After stirring at room temperature for ten minutes, the solution was diluted with water (20 ml) and extracted 3 times with 15 ml each of ethyl acetate. The combined extracts were dried over sodium sulfate and evaporated to afford a homogeneous solid of BU-3292T B (17 mg).

We claim:

1. The compound BU3292T A having the formula

2. A pharmaceutical composition comprising an effective antibacterial amount of BU-3292% A in combination with an inert pharmaceutically acceptable carrier or diluent.

3. A method for therapeutically treating an animal host affected by a bacterial infection which comprises administering to said host an effective antibacterial dose of BU-3292T A.

* * * * *